(12) United States Patent
Soni et al.

(10) Patent No.: US 6,645,505 B2
(45) Date of Patent: Nov. 11, 2003

(54) REPORTER GENE BASED METHOD FOR THE SCREENING OF ANTI-TUBERCULOSIS DRUGS BY USING ESSENTIAL AND REGULATORY GENES OF MYCOBACTERIA AS DRUG TARGET

(75) Inventors: Vishal Soni, Chandigarh (IN); Lakshami Pathi Khandrika, Chandigarh (IN); Pushpa Agrawal, Chandigarh (IN)

(73) Assignee: Council of Scientific and Industrial Research, New Delhi (IN)

( * ) Notice: Subject to any disclaimer, the term of this patent is extended or adjusted under 35 U.S.C. 154(b) by 8 days.

(21) Appl. No.: 09/818,236

(22) Filed: Mar. 27, 2001

(65) Prior Publication Data

US 2002/0164573 A1 Nov. 7, 2002

(51) Int. Cl.$^7$ .................... A61K 39/04; A61K 39/02; A61K 39/00
(52) U.S. Cl. ................ 424/248.1; 424/9.1; 424/9.2; 424/184.1; 424/185.1; 424/190.1; 424/200.1; 530/300; 530/350; 536/23.1; 536/23.7
(58) Field of Search .................. 424/9.1, 9.2, 184.1, 424/189.1, 190.1, 200.1, 248.1; 530/300, 350; 536/23.1, 23.7

*Primary Examiner*—Rodney P Swartz
(74) *Attorney, Agent, or Firm*—Ladas & Parry

(57) ABSTRACT

The present invention relates to a method for making recombinant *Saccharomyces cerevisiae*. The method includes the steps of amplifying one or more whiB-like genes of Mycobacteria by polymerase chain reaction (PCR), cloning the amplified one or more whiB-like genes into a plasmid, transforming the clone into an *E. coli* using a first shuttle vector, amplifying the clone, introducing the amplified clone into a second shuttle vector, introducing said second shuttle vector into *Saccharomyces cerevisiae*.

16 Claims, No Drawings

REPORTER GENE BASED METHOD FOR THE SCREENING OF ANTI-TUBERCULOSIS DRUGS BY USING ESSENTIAL AND REGULATORY GENES OF MYCOBACTERIA AS DRUG TARGET

FIELD OF THE INVENTION

This invention relates to the development of a reporter gene based drug screening system against tuberculosis by using essential regulatory genes of Mycobacterium tuberculosis H37Rv as a target. Such regulatory genes are more particularly, the whiB genes of mycobacteria whose functions are essential for the survival and normal growth of mycobacteria.

BACKGROUND OF THE INVENTION

The Streptomycetes are dimorphic organisms. After reaching the late log phase of growth, the substrate mycelia differentiate into the aerial mycelia. The tip of the aerial mycelium then differentiates into a chain of spores. Each spore represents a single cell and is separated by a septum. In 1992, Davis and Chater (Davis, N. K. and Chater, K. F. 1992. Mol. Gen. Genet: 232: 352–358) reported that any mutation in the whiB gene of *Streptomyces coelicolor* A3(2) results into a non sporulating organism. These mutants were also white in colour since they had lost capability-to, produce deep reddish blue pigment which is a characteristic of the wild type strain of *Streptomyces coelicolor* A3(2). It was further confirmed that a fully functional whiB gene is essential for the sporulation of the *Streptomyces coelicolor* A3(2) and whiB gene may be a transcription activator. A whiB homologue was also reported from Streptoverticillium sps, *Streptomyces aurofaciens* and Rhodococcus opacus (Kormanec and Homerova, 1993 Nucl. Acid Res. 21:2512; Seibert,V., Kourbatova, E. M., Golowela, L. M. and M. Schlomann. 1998. 180:3503–3508; Soliveri, J. E., Vijg nboom, E., Granozzi, C., Plaskitt, K. A. and K. F. Chater. 1993. J.Gen.Microbiol. 139:2569–2578). However, unexpectedly, the genome sequence of *Mycobacterium tuberculosis* H37Rv showed the presence of four genes that is whiBI/Rv3219–254 bp, whiB2/Rv3260c-269 bp, whiB3/Rv 3416–308 bp and whiB4/Rv3681 c-302 bp whose deduced amino acid products were similar to the whiB gene of *Streptomyces coelicolor* A3(2). The amino acid sequences of whiB genes of *M. tuberculosis* H37Rv show 32–35 percent homology to the amino acid sequences of Streptomyces whiB genes. Although the homology is relatively low, the general property of the predicted protein remains conserved. General morphology of mycobacteria is bacillus, unlike the species of streptomycetes, which are filamentous. So far, sporulation of mycobacteria has not been reported. Therefore, the presence of whiB like genes, which controls the sporulation, in a non-sporulating organism is highly intriguing. The predicted amino acid sequence of whiB gene suggests that the whiB gene may code for a transcription activator. If that were so, then whiB genes would be a regulatory gene. However, so far it has not been reported that the whiB genes indeed code for a transcription activator, If the whiB genes are indeed a set of regulatory genes then the question is what kind of genes do they control? Recently, Gomez and Bishai (Gomez, J. E. and Bishai, W. R., 2000. Proc. Nati. Acad. Sci. 97: 8554–8559) have shown that a whiB2 homologue of *Mycobacterium tuberculosis* H37Rv is present in *Mycobacterium smegmatis* and is essential for its survival. *Mycobacterium smegmatis* is a fast growing and non-pathogenic organism. However no report or patent could be found related to the invention described in this application.

The present invention describes that out of the four whiB genes originally described in the *Mycobacterium tuberculosis* H37Rv genome sequence, the whiB1/Rv 3219 is essential to the survival of the *Mycobacterium bovis* BCG and whiB3/Rv 3416 appears to control septa formation during cell division. The properties of these genes were not reported in the genome sequence of *Mycobacterium tuberculosis* H37Rv nor have they been published in the literature (Cole et al. Nature 1998. 393: 537–544.).

Tuberculosis is still one of the major killers of human lives in India and in most of the developing countries. The spread of HIV has compounded the problems of tuberculosis because several species of mycobacteria, which were otherwise not known to infect humans, have also been found to be associated with the HIV infected patients. More than often these new pathogens are not sensitive to the conventional therapy of tuberculosis. Further the incidence of the tuberculosis caused by the drug resistant mycobacteria are also increasing at an alarming rate. These resistant bacteria do not respond to conventional therapy. Thus there is need to find either new drugs or first to find new drug targets that have not yet developed the capability to modify themselves and then search for a drug, which would attack at a particular target. The search for a new drug without any specific target usually leads to the rediscovery of known drugs. Secondly, the mode of action of the new drug discovered by random search is usually not known, thus the study of pharmacokinetics can be a laborious process. Further, if the organism develops resistance to the new drug then modification of these drugs which, would suit to the target of resistant organism would be very difficult. With the advancement in computer simulation studies and modeling software, it is possible to design a drug if the target is known.

The present invention uses the DNA binding property of the whiB genes of *Mycobacterium tuberculosis* H37Rv that has been demonstrated for the first time in this invention. The invention is based on the activation of the reporter gene lacZ, which produces the enzyme β-galactosidase. In a normal circumstance the β-galactosidase activity remain repressed because the whiB genes, which code for a DNA binding protein, can bind to the lexA operators present in certain strains of *Saccharomyces cerevisiae* as well as in reporter plasmids. Binding of whiB gene products with the operator's sequence results in the repression of the transcription of the lacZ gene, which produces β-galactosidase enzyme. However if a drug binds to the whiB genes then its products will not be available for binding to the operators and the lacZ transcription will continue. Activation or repression of β-galactosidase can be monitored either by adding 5-Bromo-4-chloro-3-indolyl β-D-galactopyranoside (X-gal) into the growth medium, which produces blue color or by adding o-nitrophenol β-D-galactopyranoside (ONPG) which produces yellow color in presence of β-galactosidase. Intensity of the color production is directly related to the activation of β-galactosidase enzyme and therefore would be directly related to the binding capability of a drug. In other words, a strong binder to the target will allow strong activation of β-galactosidase, however, a poor binder to the target would permit low activation of β-galactosidase enzyme. The method in this invention is fully compatible to any automated High-Through-Put screening system or any other automated or non-automated screening system.

The present invention is thus based upon the need to find a new drug target in *Mycobacterium tuberculosis* H37Rv and develop a drug screening system based upon the identified target. To suit the fast developing technology and the urgent need to find a better cure, it is desired that the screening system is compatible to any automated High-Through-Put screening or any other mechanised screening procedure.

OBJECTS OF THE INVENTION

The main objective of the present invention is to provide a new drug target, which would facilitate target specific screening of anti-tuberculosis drugs.

Another objective of the present invention is to develop a drug screening system, which is fast and uses the properties of the target gene.

SUMMARY OF THE INVENTION

The present invention relates to a drug screening method taking advantage of the yeast two-hybrid system, known in the literature. The invention also describes that the whiB genes are essential regulatory genes of *Mycobacterium tuberculosis* H37Rv and appear to be conserved amongst the pathogenic and slow growing mycobacteria. Thus the novelty of the method of the invention is to use the whiB genes which are regulatory genes of mycobacteria, whose functions have not been reported so far, as drug target by using the yeast *Saccharomyces cerevisiae* as a surrogate host.

DETAILED DESCRIPTION OF THE INVENTION

To accomplish the aforesaid and other objectives, it is essential to demonstrate that a functional target gene is essential for the survival of the *Mycobacterium tuberculosis* H37Rv. The sporulation gene homologue of *Streptomyces coelicolor* A3(2) was found to be present in *Mycobacterium tuberculosis* H37Rv. Since mycobacteria are not known to sporulate, it was assumed that these sporulation homologues would have yet unknown but important function. It has been assumed that the whiB genes may act, as a transcription activator and therefore would have regulatory function. It is further assumed that a regulatory gene, which controls sporulation, yet present in a non-sporulating organism, may indeed be an essential gene.

The drug screening method described in this invention takes advantage of the yeast two-hybrid system known in the literature. The invention also describes that the whiB genes are essential regulatory genes of *Mycobacterium tuberculosis* H37Rv and appear to be conserved amongst the pathogenic and slow growing mycobacteria. Thus the novelty of the invention is to use the whiB genes which are regulatory genes of mycobacteria, whose function have not been reported so far, as a drug target by using the yeast *Saccharomyces cerevisiae* as a surrogate host.

*Mycobacterium tuberculosis* H37Rv is a slow growing organism and is highly virulent. Thus, the use of live organism poses a severe health hazard. Therefore, it was essential to develop a screening system in a different host organism, which is nonpathogenic, fast growing and also to provide a method that is adaptable to High-Through-Put screening or any other automated screening systems.

Accordingly, the invention provides a reporter gene based method for the screening of anti-tuberculosis drugs comprising using whiB like genes (whiB1, whiB2 whiB3 whiB4) present in *Mycobacterium tuberculosis* H37Rv, *Mycobacterium bovis* BCG and *Mycobactereium leprae* having DNA and protein sequence as shown in sequence ID 1 to 4 as drug targets for the screening of anti-tuberculosis and anti-leprosis drugs.

The whiB3 gene of *Mycobacterium tuberculosis* H37Rv and *Mycobacterium bovis* BCG can be used for the screening of anti-tuberculosis drugs. The presence of functional whiB4 gene of *Mycobacterium tuberculosis* H37Rv and *Mycobacterium bovis* BCG is important for their normal growth. The whiB4 gene of *Mycobacterium tuberculosis* H37Rv and *Mycobacterium bovis* BCG code for a DNA binding protein. The drugs against whiB2 and the whiB4 genes of *Mycobacterium tuberculosis* H37Rv and *Mycobacterium bovis* BCG will be particularly useful where drug resistance has developed against the whiB1 and whiB3 genes or where the anti-whiB1 and anti-whiB3 drugs are allergic or toxic. The source of whiB like genes can be *Mycobacterium avium, Mycobacterium fortuitum, Mycobacterium gastri, Mycobacterium kansasii, Mycobacterium leprae, Mycobacterium marinum, Mycobacterium microti, Mycobacterium phlei, Mycobacterium scrofulaceum, Mycobacterium smegmatis* and *Mycobacterium xenopi* and related organisms.

Further, the present invention provides for a reporter gene based method for the screening of anti-tuberculosis drugs by using essential and regulatory genes of mycobacteria as a drug target and comprises the following steps:

(a) amplifying the whiB genes of Mycobacterium tuberculosis H37Rv by polymerase chain reaction (PCR);

(b) cloning the products obtained in step (a) into plasmid vectors such as pUC19 or pBluescript $SK^+$ or $SK^-$ and transforming into *E. coli;*

(c) amplifying whiB genes of *Mycobacterium bovis* BCG by using the oligonucleotide primers of *Mycobacterium tuberculosis* H37Rv;

(d) cloning the product obtained in step (c) into a plasmid vector pUC19 or pBluescript $SK^+$ or $SK^-$; and sequencing the products to confirm the sequence of cloned fragment;

(e) constructing a gene disruption integrative vector by inserting a kanamycin cassette in between the whiB gene sequences of *Mycobacterium tuberculosis* H37Rv;

(f) constructing a gene disruption integrative vector by inserting a kanamycin cassette in between the whiB gene sequences of *Mycobacterium bovis* BCG;

(g) amplifying whiB genes of *Mycobacterium tuberculosis* H37Rv by using oligonucleotide primers carrying either EcoRI, or BamHI restriction enzyme sites at the 5' end and XhoI restriction enzyme site at the 3' end;

(h) digesting the fragment as obtained in step (g) with suitable restriction enzymes and then cloning the fragment into a *E. coli/Saccharomyces cerevisiae* shuttle vector pEG202 to produce the cloned gene as a LexA fusion protein and transforming the recombinant plasmid into *E. coli;*

(i) preparing large amount of the desired recombinant plasmid and then transforming the recombinant whiB1, whiB2, whiB3, and whiB4/pEG202 into the *Saccharomyces cerevisiae* strains EGY48 and EGY191, (j) co-transforming the pJK101, pSH 18–34, pSH17-4, pJG4–5 and pRFHM vectors into the *Saccharomyces cerevisiae* strains EGY48 and EGY191 already harboring whiB genes in the pEG202 vector and then selecting for the clones, which complements for uracil and histidine+uracil or histidine+uracil+tryptophan auxotrophy;

(k) growing the *Saccharomyces cerevisiae* transformants in the yeast nitrogen base medium containing: galactose/raffinose+, ura–, BU salt+, X-gal+; his–, ura–, BU salt+, X-gal+, glucose; galactose/raffinose+, ura–, his–, leu–; glucose+, ura–, his–, leu–; galactose/raffinose+, ura–, his–, trp–, leu– and glucose+, ura–, his–, trp–, leu– plates, and (l) using the DNA binding property of the whiB1, whiB2 and whiB3 for the screening of anti-tuberculosis drugs.

In an embodiment, the restriction enzymes are selected from EcoRI, XmaI BamHI, SalI, NcoI, NotI, XhoI, SalI and PstI.

In another embodiment, whiB1 gene is essential for the survival of *Mycobacterium tuberculosis* H37Rv and *Mycobacterium bovis* BCG.

In still another embodiment, the whiB2 gene is essential for the normal growth of *Mycobacterium tuberculosis* H37Rv and *Mycobacterium bovis* BCG.

In yet another embodiment, the whiB3 gene is essential for the cell division of a *Mycobacterium tuberculosis* H37Rv and *Mycobacterium bovis* BCG.

In an embodiment, the whiB4 gene is essential for the normal growth of *Mycobacterium tuberculosis* H37Rv and *Mycobacterium bovis* BCG.

In another embodiment, the whiB4 gene of *Mycobacterium tuberculosis* H37Rv and *Mycobacterium bovis* BCG is a transcription activator.

In yet another embodiment, the whiB1, whiB2 and whiB3 genes of *Mycobacterium tuberculosis* H37Rv and *Mycobacterium bovis* BCG code for a DNA binding protein.

In still another embodiment, the whiB1, whiB2 and whiB3 genes of *Mycobacterium tuberculosis* H37Rv and *Mycobacterium bovis* BCG repress the activation of β-galactosidase genes after binding to the Lex A operator or any other like operators.

In an embodiment, the DNA binding domain of the whiB genes is situated within the 15 amino acids at the carboxy-terminus of the protein.

In another embodiment, the DNA binding property of the whiB genes has been used to screen those anti-tuberculosis drugs which attack the whiB genes. The method of the invention can be used for any gene, which codes for a DNA binding protein. The method is compatible to any High-Through-Put or automated screening system.

The details of the invention are:

The *Mycobacterium tuberculosis* H37Rv genome sequence was obtained from the internet site http://www.sanger.ac.uk and the sequence of the whiB genes were recovered. The authors, (Cole et al. Nature, 1998:393, 537–543) have annotated these genes as: whiB1/Rv3219 (255 bp), whiB2/Rv3260c (270 bp), whiB3/Rv3416 (309 bp) and whiB4/Rv3681c (303 bp). The sequence of oligonucleotide primers designed to amplify the whiB genes were as follow:

F 5' acccgttaccagccaagaag 3' and R 5' gggacggttgatgctgtag 3' for whiB1

F5' ggccgggtcagatgatc 3' and R 5'accgcatctgagtttgg 3' for whiB2

F 5' atgccacagccggagcagctac 3' and R 5' ttaagctgtgcggcg-gatgcc 3' for whiB3

F 5' ctatccggcggtgccggtgcg 3' and R 5' gtggtacgcagcgta-gacgcg 3' for whiB4

The sequences of the genes are shown as sequences ID 1 to 4 separately.

The PCR was done by standard procedure. The PCR products were separated on 1 percent agarose gel and the amplified bands were removed by cutting the gel. The PCR amplified DNA was purified by using a commercially available purification kit. Cloning and then transformation of the PCR fragments were done by standard procedure. The sequence of cloned fragments was confirmed by standard procedure.

Once the identity of the cloned fragments was confirmed, the *Mycobacterium tuberculosis* H37Rv whiB genes were used as probe to check whether similar genes were present in the *Mycobacterium bovis* BCG or not. The *Mycobacterium bovis* BCG chromosomal DNA was prepared by a published method (G. P. S. Raghava, R. J. Solanki, V. Soni and P. Agrawal. Biotechniques. 2000. 29:108–116). A standard Southern hybridization protocol was followed to confirm the presence of whiB genes in *Mycobacterium bovis* BCG as well.

As described for the Mycobacterium tuberculosis H37Rv, all four whiB genes in *Mycobacterium bovis* BCG were also PCR amplified. The oligonucleotide primers and PCR conditions were identical in both the cases. The PCR products were separated in an agarose gel, purified, cloned and sequenced as described in case of *Mycobacterium tuberculosis* H37Rv.

The sequence alignment using commercial computer software confirmed that the whiB gene sequences of *Mycobacterium tuberculosis* H37Rv and *Mycobacterium bovis* BCG are identical.

By using commercially available computer software Gene-Runner, restriction enzymes sites within the whiB sequences were found. Based on the sequence analysis results following enzyme sites were selected to generate vectors that can be used for gene disruption in *Mycobacterium bovis* BCG by the process of homologous recombination.

To generate a vector, which could be used for gene disruption the following constructs were created:

(a) for the whiB1, kanamycin cassette was inserted at PvuII site;

(b) for whiB2, two independent constructs were made at MluI and at HaeIII sites;

(c) for whiB3, two constructs were made at EcoRI site and at the ClaI site;

(d) for whiB4, at the SacII site.

The whiB recombinant clones were digested with restriction enzymes. However, whenever the recombinant clone had more than one site for a particular enzyme then the purified whiB fragments were digested and then ligated with the kanamycin cassette, which codes for kanamycin resistance. The *E. coli* strain was transformed and clones were selected for ampicillin and kanamycin resistance. Since these clones do not have mycobacterial origin of replication they will not survive within the mycobacteria unless they are integrated in the mycobacteria genome. Electro-competent *Mycobacterium bovis* BCG cells were prepared using the art known in the literature and transformed with lptg of purified vector DNA. In each tube imi of 7H9 Middlebrook's medium was added and incubated at 37° C. for 48 hrs. The culture was then plated on a 7H 10 Middlebrook's medium containing both ampicillin and kanamycin and incubated at 37° C. After three weeks of growth the colonies were again plated on kanamycin plates and allowed to grow at 37° C. In the kanamycin plates, the colonies could be seen only after 6 weeks of incubation which suggested that the whiB disruption is deleterious for the growth of *Mycobacterium bovis* BCG. Disruption of individual whiB genes had the following effects on the growth and survival of *Mycobacterium bovis* BCG:

1. the whiB1 disruption is lethal.
2. the whiB2 disruption makes the cells very slow growing and the colonies are very small in size.
3. the whiB3 disruption makes the cells mycelial which clearly suggests that this disruption is controlling septa formation.
4. the whiB4 disruption also had similar effect like whiB2 disruption.

To demonstrate the nature of the whiB gene, yeast two-hybrid system was used. This art is well known in the literature. In principle the system has been developed in such way that the trans-activation domain and the DNA binding domains are in two different plasmids. Unless both domains come together, protein-protein interaction will not take place thus a gene will not get activated. However, the system also allows one to check whether the gene in question codes for DNA binding protein or a transcription activator.

The whiB1, whiB2 and whiB4 genes were PCR amplified using oligonucleotide primers, which had EcoRI site at their 5' end and XhoI site at their 3' end. The whiB3 gene was amplified with the primers having BamHI site at the 5' end and XhoI site at the 3' end. After digesting with the appropriate restriction enzymes these genes were cloned into the *E. coli/Saccharomyces cerevisiae* shuttle vector pEG202. After selecting for ampicillin resistant colonies, the recombinant clones were selected for his⁻ colonies in *Saccharomyces cerevisiae* EGY 48 and EGY 191. The his– clones were then transformed with the plasmids: pJk101, pSH18–34, pJG4–5, and pRFHM either singly or in combinations. The clones which complemented either for uracil, uracil+histidine or uracil+histidine+tryptophan were selected. These clones were then tested for either activation or repression of β-galactosidase activity by growing them in the plates containing yeast-nitrogen based medium and following supplements:

(1) glucose⁺, ura⁻ BU salt⁺+X-gal (no color)
(2) galactose/raffinose⁺, ura⁻+BU salt⁺+X-gal (no color by all the four whiB genes only when pJK101 is present but pJK101 produced bright blue color, suggesting that whiB genes are expressed in the *Saccharomyces cerevisiae* and repress the activation of lacZ gene.)
(3) glucose⁺, ura⁻,his⁻,leu⁻ (no growth)
(4) galactose/raffinose⁺, ura⁻, his⁻, leu⁻ (no growth of whiB1, whiB2, and whiB3 but some growth was seen of whiB4 in presence of pSH18–34)
(5) galactose/raffinose+, ura–, his–, tryp–, leu– (only whiB4 showed some growth after three days of incubation in presence of pSH18–34 and pJG4–5, suggesting that the whiB4 gene is a weak transcription activator)
(6) glucose+, ura–, his–, tryp–, leu– (no growth).

The method of the present invention is illustrated in the examples given below which should not, however, be construed to limit the scope of the present invention.

EXAMPLE 1

The *Mycobacterium tuberculosis* H37Rv chromosomal DNA was prepared as following a published method (G. P. S. Raghava, R. J. Solanki, V. Soni and P. Agrawal. Biotechniques. 2000. 29: 108–116).

All four whiB genes of *Mycobacterium tuberculosis* H37Rv were PCR amplified using a standard protocol. The oligonucleotide primer's and PCR conditions were as follows: F 5' acccgttaccagccaagaag 3' and R 5' gggacggttgatgctgtag 3' for whiB 1 F 5' ggccgggtcagatgatc 3' and R 5 ' accgcatctgagtttgg 3' for whiB2 F 5' atgccacagccggagcagctac 3' and R 5' ttaagctgtgcggcggatgcc 3' for whiB3 F 5' ctatccggcggtgccggtgcg 3' and R 5' gtggtacgcagcgtagacgcg 3' for whiB4

The PCR products were separated on 1 percent agarose gel and the amplified bands were removed by cutting the gel. The PCR amplified DNA was purified by using a commercially available kit.

The ends of the purified DNA were phosphorylated using T4 Pol-Kinase and then cloned into the SmaI site of the dephosphorylated pUC19 vector. The recombinant plasmids were transformed into *E. coli* strain and selected for the colonies, which did not produce blue color. The white colonies were recovered from the plates and were grown on a fresh medium containing 100 ug/ml ampicillin and 25 ug/ml of kanamycin as a selection marker. The clones were sequenced using a standard method, well known in the art. Thus this example establishes the cloning and confirmation of the four whiB genes of *Mycobacterium tuberculosis* H37Rv.

EXAMPLE 2

The *Mycobacterium tuberculosis* H37Rv is a highly virulent strain. Therefore, in order to find a suitable working system a non-virulent but vaccine strain of *Mycobacterium bovis* BCG was checked for the presence of whiB homologues. Genomic DNA of *Mycobacterium bovis* BCG was digested with SacI and BamHI restriction enzymes and the DNA fragments were separated on an 1 percent agarose gel. The DNA was transferred onto a Hybond Nylon membrane using the published protocol and then the DNA was fixed in the membrane at 80° C. for 30minutes. The cloned whiB fragments from pUC 19 were removed by XbaI and KpnI digestion and the DNA was purified using an Gel Extraction kit. The purified fragments were then used for $32_P$ dCTP labeling by random priming kit, which is commercially available. By using standard protocol of Southern hybridization it was confirmed that the four whiB genes homologues of *Mycobacterium tuberculosis* H37Rv are present in *Mycobacterium bovis* BCG. The four whiB genes of *Mycobacterium bovis* BCG were PCR amplified using oligonucleotide primers of *Mycobacterium tuberculosis* H37Rv. The PCR fragment were cloned and transformed into a *E. coli* strain as described for *Mycobacterium tuberculosis* H37Rv. The DNA sequence of the cloned fragment and sequence alignment using commercial computer software confirmed that the whiB gene sequence of *Mycobacterium tuberculosis* H37Rv and *Mycobacterium bovis* BCG is identical.

EXAMPLE 3

In order to demonstrate the function of whiB genes in the life cycle of mycobacteria, the four-whiB homologues were disrupted in *Mycobacterium bovis* BCG. By using commercially available computer software Gene-Runner, restriction enzymes sites within the whiB sequences were found. Based on the sequence analysis results, following restriction enzyme sites were selected to generate vectors that then can be used for gene disruption in *Mycobacterium bovis* BCG by the process of homologous recombination. To generate a vector, which could be used for gene disruption the following constructs were created:

(a) for the whiB1, kanamycin cassette was inserted at PvuII site at the position 143;

(b) for whiB2, two independent constructs were made at M/uI at the position 138 and at HaeIII at the position 133;

c) for whiB3, two constructs were made EcoRI site at the position 52, and at the C/al site at the position 85;

(d) for whiB4, insertion was at the SacII site at position 192.

The whiB recombinant clones were digested with the restriction enzymes, however, whenever the recombinant clone had more than one site for a particular enzyme then the purified whiB fragments were digested and then ligated with the kanamycin cassette, which codes for kanamycin resistance. The *E. coli* strain was transformed and clones were selected for ampicillin and kanamycin resistance. Since these clones do not have mycobacterial origin of replication, they will not survive within the mycobacteria unless they are integrated in the mycobacteria genome. Electro-competent *Mycobacterium bovis* BCG cells were prepared using the art known in the literature and transformed with 1 µg of purified vector DNA. In each tube, 1 ml of 7H9 Middlebrook's medium was added and incubated at 37° C. for 48 hrs. The culture was then plated on a 7H10 Middlebrook's medium containing both ampicillin and kanamycin and incubated at 37° C. After three weeks of growth, the colonies were again plated on only kanamycin plates and allowed to grow at 37° C. In the kanamycin plates, the colonies could be seen only after 6 weeks of incubation which suggested that the whiB disruption is deleterious for the growth of *Mycobacterium bovis* BCG. Disruption of individual whiB genes had the same effects on the growth-and survival of *Mycobacterium bovis* BCG.

EXAMPLE 4

To demonstrate the nature of the whiB gene, the yeast two-hybrid system was used. This art is well known in the literature. In principle, the system has been developed where trans-activation domain and the DNA binding domains are in two different plasmids. Unless they come together, protein-protein interaction will not take place thus a gene will not get activated. However, the system also allows one to check whether the gene in question codes for DNA binding protein or a transcription activator.

The three whiB genes: whiB1, whiB2 and whiB4 were PCR amplified with oligonucleotide primers which had EcoRI site sequence in the 5' end and XhoI site sequence on their 3' end. The whiB3 gene was amplified using BamHI site in its 5' end because the whiB 3 gene has an internal EcoRI site. The PCR conditions were as described earlier. The PCR products were purified using a commercial purification kit and digested either with EcoRI and XhoI or BamHI and XhoI restriction enzymes. The *E. coli/ Saccharomyces cerevisiae* shuttle vector pEG202 was also digested appropriately, dephosphorylated and the PCR fragments were ligated into the vector by the method well known in the literature. The recombinants were selected on an ampicillin plate. The ampicillin positive clones were hybridized using the whiB genes as probes by the method well established in the literature. Plasmids were recovered from the clones that gave positive signal by using published method. To establish further that the correct gene has been cloned, the plasmids were digested with appropriate restriction enzymes as described earlier and checked on an agarose gel for the correct size fragment.

Using a commercially available purification kit, large-scale plasmid preparation of the recombinant clones was made. Using a published protocol, 1 μg of the recombinant plasmid was transformed into *Saccharomyces cerevisiae* EGY48 and EGY191 strains and selected for the complementation of histidine auxotrophy. The clones were patched on a histidine negative plate. The *Saccharomyces cerevisiae* EGY48 and EGY191 strains carrying recombinant whiB genes were co-transformed using various combinations of the plasmids:

(a) recombinant pEG202+pSH18–34+pJG4–5 (selected for histidine, uracil and tryptophan auxotrophy)
(b) pSH17-4+pSH18–34+pJG4–5 (selected for uracil and tryptophan auxotrophy)
(c) pRFHM1+pSH18–34+pJG4–5 (selected for uracil and tryptophan auxotrophy)
(d) recombinant pEG202+pJk101 (selected for histidine and uracil auxotrophy)
(e) pRFHM1+pJK101 (selected for uracil auxotrophy)
(f) pJK101 (selected for uracil auxotrophy)
(g) recombinant pEG202+pSH18–34+pJG4–5 (selected for histidine, uracil and tryptophan auxotrophy).

Once the transformants complementing for the right auxotrophy were obtained, these clones were sub-cultured on a selective medium lacking those amino acids which was coded by the plasmids. Randomly selected six different clones were then streaked on the medium having following combinations:

(1) glucose$^+$, ura$^-$ BU salt$^+$+X-gal
(2) galactose/raffinose$^+$, ura$^-$+BU salt$^+$+X-gal
(3) glucose$^+$, ura$^-$,his$^-$,leu$^-$
(4) galactose/raffinose$^+$, ura$^-$, his$^-$, leu$^-$
(5) galactose/raffinose+, ura–, his–, tryp–, leu–
(6) glucose+, ura–, his–, tryp–, leu–.

The plates containing X-gal were covered with aluminum foil to protect from light and were incubated at 30° C. for 18–24 hrs.

The whiB1, whiB2 and whiB3 genes in the combination number (g) did not produce any blue color in an X-gal+, galactose/raffinose+, ura–, BU+ plates nor did it grow on galactose/raffnose+, ura–, his-, tryp- leu-plates. These combinations also did not induce leucine prototrophy. In contrast, the combination (d) repressed the lacZ induction when it was grown on an ura-, galactose/raffinose+, BU+, X-gal+ plates, because they did not produce blue color, however, the pJk101 alone (combination- f) produced blue color. These results confirmed that the whiB1, whiB2 and the whiB3 genes code for a DNA binding protein but not transcription activator.

The whiB4 gene is a weak transcription activator because unlike the recombinant whiB1, whiB2, and whiB3, the recombinant whiB4 in the combination number (g) produced light blue color in an X-gal+, galactose/raffinose+, ura–, BU+ plates and also showed a weak activation of leucine prototrophy. This example establishes that the mycobacteria regulatory genes can be studied in an eukaryotic system—that is yeast and the whiB genes of the *Mycobacterium tuberculosis* H37Rv and *Mycobacterium bovis* BCG either code for DNA binding protein or a transcription activator.

EXAMPLE 5

To check whether whiB like genes are present in other species of mycobacteria or not, the following species of the mycobacteria were tested for the presence of whiB like genes: *Mycobacterium avium, Mycobacterium fortuitum, Mycobacterium gastri, Mycobacterium kansasii, Mycobacterium marinum, Mycobacterium microti, Mycobacterium phlei, Mycobacterium scrofulaceum, Mycobacterium smegmatis* and *Mycobacterium xenopi* using standard and published information. Except in *Mycobacterium fortuitum* which appear to have only whiB1 homologue, the whiB genes homologues are present in all the species listed. The results suggest that one can use the whiB genes of the above species as well to develop a drug target.

ADVANTAGES OF THE PRESENT INVENTION

1. The invention provides that the whiB genes of the *Mycobacterium tuberculosis* H37Rv and *Mycobacterium bovis* BCG are regulatory genes.

2. The invention described herein also provides that the disruption of whiB genes is either lethal or deleterious for the survival of mycobacteria.
3. The invention also provides that the whiB genes are used as drug target to search for anti-tuberculosis drugs.
4. The invention described herein provides that the yeast two-hybrid system can be used to study the mycobacterial regulatory genes and then to study to what genes are controlled by these regulatory genes.
5. This invention is the first report where yeast two-hybrid system has been used to investigate the nature of a protein of *Mycobacterium tuberculosis*, which so far, had only predicted function.
6. This invention also provides for a method wherein all genetically engineered but truncated regulatory genes can also be studied. These studies are done to delineate the function of different regions of the regulatory genes.
7. The invention also provides means to study protein-protein interactions of mycobacterial genes in a heterologous host that is not infectious thus does not pose a health hazard or demand special laboratory set-up.
8. The invention described herein is a reporter gene based assay that uses a well-characterized gene lacZ. The lacZ gene codes for the β-galactosidase. The assay of β-galactosidase enzyme is simple, thus the method is also HTS compatible.

What is claimed is:

1. A method for making a recombinant *Saccharomyces cerevisiae* said method comprising the steps of:

a) amplifying one or more whiB-like genes of Mycobacteria by polymerase chain reaction (PCR), wherein the whiB-like genes are selected from the group consisting of whiB1 (SEQ ID NO:1), whiB2 (SEQ ID NO:3), whiB3 (SEQ ID NO:5), and whiB4 (SEQ ID NO:7) and the Mycobacteria are selected from the group consisting of *Mycobacterium tuberculosis, Mycobacterium bovis, Mycobacterium avium, Mycobacterium fortuitum, Mycobacterium gastri, Mycobacterium kansasii, Mycobacterium leprae, Mycobacterium marinum, Mycobacterium microti, Mycobacterium phlei, Mycobacterium scrofulaceum, Mycobacterium smegmatis*, and *Mycobacterium xenopi,* b) cloning the amplified one or more whiB-like genes into a plasmid, c) transforming the clone into an *E. coli* using a first shuttle vector, d) amplifying the clone, e) introducing the amplified clone into a second shuttle vector, f) introducing the second shuttle vector into *Saccharomyces cerevisiae, and* g) obtaining transformed *Saccharomyces cerevisiae.*

2. The method as claimed in claim 1, wherein *Saccharomyces cerevisiae* is a strain selected from EGY 48 or EGY 191.

3. The method as claimed in claim 1, wherein the plasmid is selected from the group consisting of pUC19, pBluescript $SK^+$, and pBluescript $SK^-$.

4. The method as claimed in claim 1, wherein the whiB genes are amplified with primers carrying either EcoRI, or BamHI restriction enzyme sites at the 5' end and XhoI restriction enzyme site at the 3' end.

5. The method as claimed in claim 1, wherein the first shuttle vector is pEG202.

6. The method as claimed in claim 1, wherein the whiB1 gene is amplified using primers F 5' acccgttaccagccaagaag 3' (SEQ ID NO:9) and R 5' gggacggttgatgctgtag 3' (SEQ ID NO:10).

7. The method as claimed in claim 1, wherein the whiB2 gene is amplified using primers F 5' ggccgggtcagatgatc 3' (SEQ ID NO: 11) and R 5' accgcatctgagtttgg 3' (SEQ ID NO:12).

8. The method as claimed in claim 1, wherein the whiB3 gene is amplified using primers F 5' atgccacagccggagcagctac 3' (SEQ ID NO:13) and R 5' ttaagctgtgcggcggatgcc 3' (SEQ ID NO:14).

9. The method as claimed in claim 1, wherein the whiB4 gene is amplified using primers F 5' ctatccggcggtgccggtgcg 3' (SEQ ID NO:15) and R 5' gtggtacgcagcgtagacgcg 3' (SEQ ID NO:16).

10. The method as claimed in claim 1 the one or more amplified whiB-like genes prepared in step a) is digested with one or more restriction enzymes.

11. The method as claimed in claim 10, wherein the one or more restriction enzymes are selected from a group consisting of EcoRI, XmaI BamHI, Sail, NcoI, NotI, XhoI, SalI, and PstI.

12. The method as claimed in claim 1, wherein genes comprising whiB1, whiB2, and whiB3 express DNA-binding proteins.

13. The method as claimed in claim 1, wherein gene whiB4 is a transcription activator.

14. The method as claimed in claim 1, wherein the DNA binding domain of the whiB genes is located within the 15 amino acids from the C-terminus of the protein.

15. The method as claimed in claim wherein the DNA-binding proteins repress the activation of β-galactosidase.

16. The method as claimed in claim 1, wherein the assay system is compatible with a High-Through-Put or automated screening system.

* * * * *

SEQUENCE LISTING

<160> NUMBER OF SEQ ID NOS: 16

<210> SEQ ID NO 1
<211> LENGTH: 255
<212> TYPE: DNA
<213> ORGANISM: Mycobacterium tuberculosis
<220> FEATURE:
<223> OTHER INFORMATION: whiB1 gene of Mycobacterium tuberculosis H37Rv

<400> SEQUENCE: 1

```
atggattggc gccacaaggc ggtctgtcgt gacgaggatc cggaactgtt cttcccggta      60
ggaaacagtg gtccggcact tgcgcagatc gctgacgcga aactggtctg taatcggtgc     120
ccggtcacca cagagtgcct cagctgggca ctgaataccg gccaggactc gggcgtctgg     180
ggaggcatga gcgaagacga gcggcgcgcg ctgaagcgtc gcaacgcccg cacgaaagcc     240
cgtaccgggg tctga                                                      255
```

<210> SEQ ID NO 2
<211> LENGTH: 84
<212> TYPE: PRT
<213> ORGANISM: Mycobacterium tuberculosis
<220> FEATURE:
<223> OTHER INFORMATION: Peptide sequence encoded by whiB1 gene of
      Mycobacterium tuberculosis H37Rv

<400> SEQUENCE: 2

Met Asp Trp Arg His Lys Ala Val Cys Arg Asp Glu Asp Pro Glu Leu
 1               5                  10                  15

Phe Phe Pro Val Gly Asn Ser Gly Pro Ala Leu Ala Gln Ile Ala Asp
                20                  25                  30

Ala Lys Leu Val Cys Asn Arg Cys Pro Val Thr Thr Glu Cys Leu Ser
            35                  40                  45

Trp Ala Leu Asn Thr Gly Gln Asp Ser Gly Val Trp Gly Gly Met Ser
        50                  55                  60

Glu Asp Glu Arg Arg Ala Leu Lys Arg Arg Asn Ala Arg Thr Lys Ala
65                  70                  75                  80

Arg Thr Gly Val

<210> SEQ ID NO 3
<211> LENGTH: 270
<212> TYPE: DNA
<213> ORGANISM: Mycobacterium tuberculosis
<220> FEATURE:
<223> OTHER INFORMATION: whiB2 gene of Mycobacterium tuberculosis H37Rv

<400> SEQUENCE: 3

```
tcagatgatc cgcgtttga ggcggcggcg ctcgcgttcg aaagaccac cccagatgcc      60 gaaccgctcg tcatgagcca gggcgtactc cagacactcg tgccgcacct cgcagcccat   120
gcaaatcttc ttggcctcac gcgtggagcc gcccttctcc gggaagaacg cttcgggatc   180
cgtttgcgca catagcgcac ggtcctgcca ttggtcggtg gcttccggcg cagaggttc    240 ctcgaatggc gccggcgcct cgggaaccaa                                    270
```

<210> SEQ ID NO 4
<211> LENGTH: 89
<212> TYPE: PRT
<213> ORGANISM: Mycobacterium tuberculosis
<220> FEATURE:
<223> OTHER INFORMATION: Peptide sequence encoded by whiB2 gene of
      Mycobacterium tuberculosis H37Rv

<400> SEQUENCE: 4

```
Met Val Pro Glu Ala Pro Ala Pro Phe Glu Glu Pro Leu Pro Pro Glu
 1               5                  10                  15

Ala Thr Asp Gln Trp Gln Asp Arg Ala Leu Cys Ala Gln Thr Asp Pro
            20                  25                  30

Glu Ala Phe Phe Pro Glu Lys Gly Gly Ser Thr Arg Glu Ala Lys Lys
        35                  40                  45

Ile Cys Met Gly Cys Glu Val Arg His Glu Cys Leu Glu Tyr Ala Leu
    50                  55                  60

Ala His Asp Glu Arg Phe Gly Ile Trp Gly Gly Leu Ser Glu Arg Glu
65                  70                  75                  80

Arg Arg Arg Leu Lys Arg Gly Ile Ile
                85
```

<210> SEQ ID NO 5
<211> LENGTH: 309
<212> TYPE: DNA
<213> ORGANISM: Mycobacterium tuberculosis
<220> FEATURE:
<223> OTHER INFORMATION: whiB3 gene of Mycobacterium tuberculosis H37Rv

<400> SEQUENCE: 5

```
atgccacagc cggagcagct accgggaccc aacgcagaca tctggaactg gcaattgcaa    60
ggcctgtgtc gcggcatgga ctcatcgatg ttcttccatc ccgacggcga gcgtggccgt   120
gcccgaacgc agcgcgaaca acgcgccaag gaaatgtgtc ggcgctgccc cgtgatcgag   180
gcgtgccgat cccatgcgtt agaggtcggt gagccctatg gcgtttgggg tggcctgtcc   240
gaatccgagc gcgacctact cctcaagggc accatgggac gcacccgcgg catccgccgc   300
acagcttaa                                                           309
```

<210> SEQ ID NO 6
<211> LENGTH: 102
<212> TYPE: PRT
<213> ORGANISM: Mycobacterium tuberculosis
<220> FEATURE:
<223> OTHER INFORMATION: Peptide sequence encoded by  whiB3 gene of
      Mycobacterium tuberculosis H37Rv

<400> SEQUENCE: 6

```
Met Pro Gln Pro Glu Gln Leu Pro Gly Pro Asn Ala Asp Ile Trp Asn
 1               5                  10                  15

Trp Gln Leu Gln Gly Leu Cys Arg Gly Met Asp Ser Ser Met Phe Phe
            20                  25                  30
```

```
His Pro Asp Gly Glu Arg Gly Arg Ala Arg Thr Gln Arg Glu Gln Arg
            35                  40                  45

Ala Lys Glu Met Cys Arg Arg Cys Pro Val Ile Glu Ala Cys Arg Ser
 50                  55                  60

His Ala Leu Glu Val Gly Glu Pro Tyr Gly Val Trp Gly Gly Leu Ser
 65                  70                  75                  80

Glu Ser Glu Arg Asp Leu Leu Leu Lys Gly Thr Met Gly Arg Thr Arg
                 85                  90                  95

Gly Ile Arg Arg Thr Ala
            100

<210> SEQ ID NO 7
<211> LENGTH: 303
<212> TYPE: DNA
<213> ORGANISM: Mycobacterium tuberculosis
<220> FEATURE:
<223> OTHER INFORMATION: whiB4 gene of Mycobacterium tuberculosis H37Rv

<400> SEQUENCE: 7
ctatccggcg gtgccggtgc ggcgcttgcg cttctcaagg tagtccgacc acgaaaccac    60
ctcgggatgt tgcttgagca gagccctgcg ctggcgctcg gtcatgccac cccaaacacc   120
gaactcgacc ttgttgtcca gcgcatctgc cgcacactct tgcattaccg gacagtgacg   180
gcagatcacc gcggccttgc gttgtgcggc tcctcgaaca aagagttcgt cagggtcggt   240
agtccggcac agcgccttgg atacccacgc gatccgctct ccgcgtcta  cgctgcgtac   300 cac                                                                303

<210> SEQ ID NO 8
<211> LENGTH: 100
<212> TYPE: PRT
<213> ORGANISM: Mycobacterium tuberculosis
<220> FEATURE:
<223> OTHER INFORMATION: Peptide sequence encoded by whiB4 gene of
      Mycobacterium tuberculosis H37Rv

<400> SEQUENCE: 8

Met Val Arg Ser Val Asp Ala Glu Glu Arg Ile Ala Trp Val Ser Lys
 1               5                  10                  15

Ala Leu Cys Arg Thr Thr Asp Pro Asp Glu Leu Phe Val Arg Gly Ala
            20                  25                  30

Ala Gln Arg Lys Ala Ala Val Ile Cys Arg His Cys Pro Val Met Gln
        35                  40                  45

Glu Cys Ala Ala Asp Ala Leu Asp Asn Lys Val Glu Phe Gly Val Trp
 50                  55                  60

Gly Gly Met Thr Glu Arg Gln Arg Arg Ala Leu Leu Lys Gln His Pro
 65                  70                  75                  80

Glu Val Val Ser Trp Ser Asp Tyr Leu Glu Lys Arg Lys Arg Arg Thr
                 85                  90                  95

Gly Thr Ala Gly
            100

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide primer designed to amplify the
      whiB1 gene of Mycobacterium tuberculosis H37Rv
```

```
<400> SEQUENCE: 9
acccgttacc agccaagaag                                              20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide primer designed to amplify the
      whiB1 gene of Mycobacterium tuberculosis H37Rv

<400> SEQUENCE: 10
gggacggttg atgctgtag                                               19

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide primer designed to amplify the
      whiB2 gene of Mycobacterium tuberculosis H37Rv

<400> SEQUENCE: 11
ggccgggtca gatgatc                                                 17

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide primer designed to amplify the
      whiB2 gene of Mycobacterium tuberculosis H37Rv

<400> SEQUENCE: 12
accgcatctg agtttgg                                                 17

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer designed to amplify the
      whiB3 gene of Mycobacterium tuberculosis H37Rv

<400> SEQUENCE: 13
atgccacagc cggagcagct ac                                           22

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer designed to amplify the
      whiB3 gene of Mycobacterium tuberculosis H37Rv

<400> SEQUENCE: 14
ttaagctgtg cggcggatgc c                                            21

<210> SEQ ID NO 15
<211> LENGTH: 21
<212> TYPE: DNA
<213> ORGANISM: Artificial Sequence
```

-continued

```
<220> FEATURE:
<223> OTHER INFORMATION: Description of Artificial Sequence:
      Oligonucleotide primer designed to amplify the
      whiB4 gene of Mycobacterium tuberculosis H37Rv

<400> SEQUENCE: 15
ctatccggcg gtgccggtgc g                                   21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide primer designed to amplify the
      whiB4 gene of Mycobacterium tuberculosis H37Rv

<400> SEQUENCE: 16
gtggtacgca gcgtagacgc g                                   21
```